United States Patent
Vaanhold et al.

(10) Patent No.: US 10,569,514 B2
(45) Date of Patent: Feb. 25, 2020

(54) PACKAGING FOIL COMPRISING A LUMINESCENT COMPOUND

(71) Applicant: SENSOR SPOT B.V., Wijchen (NL)

(72) Inventors: Antonius Johannes Vaanhold, Gennep (NL); Marc Jaap Staal, Slochteren (NL); Sacco Te Lintel Hekkert, Nijmegen (NL)

(73) Assignee: SENSOR SPOT B.V., Wijchen (NL)

( * ) Notice: Subject to any disclaimer, the term of this patent is extended or adjusted under 35 U.S.C. 154(b) by 107 days.

(21) Appl. No.: 15/543,245

(22) PCT Filed: Jan. 16, 2016

(86) PCT No.: PCT/NL2016/050037
§ 371 (c)(1),
(2) Date: Jul. 13, 2017

(87) PCT Pub. No.: WO2016/114667
PCT Pub. Date: Jul. 21, 2016

(65) Prior Publication Data
US 2017/0361589 A1    Dec. 21, 2017

(30) Foreign Application Priority Data

Jan. 16, 2015 (NL) .................................... 2014149

(51) Int. Cl.
*B32B 27/18* (2006.01)
*B32B 27/08* (2006.01)
*B32B 37/14* (2006.01)
*G01N 21/64* (2006.01)

(52) U.S. Cl.
CPC .............. *B32B 27/18* (2013.01); *B32B 27/08* (2013.01); *B32B 37/14* (2013.01); *G01N 21/6408* (2013.01); *G01N 21/6428* (2013.01); *B32B 2250/24* (2013.01); *B32B 2307/422* (2013.01); *B32B 2307/7244* (2013.01); *B32B 2439/40* (2013.01); *B32B 2439/70* (2013.01); *B32B 2439/80* (2013.01); *B32B 2553/00* (2013.01)

(58) Field of Classification Search
CPC ........ B32B 27/18; B32B 27/08; B32B 37/14; B32B 27/283; B32B 27/30; B32B 27/32; B32B 27/34; B32B 27/36; B32B 2250/03; B32B 2250/24; B32B 2307/422; B32B 2307/724; B32B 2307/7244; B32B 2439/40; B32B 2439/46; B32B 2439/70; B32B 2439/80; B32B 2553/00; G01N 21/6428
USPC .............................................. 428/411, 411.1
See application file for complete search history.

(56) References Cited

U.S. PATENT DOCUMENTS

| | | |
|---|---|---|
| 5,030,420 A | 7/1991 | Bacon et al. |
| 2004/0131806 A1* | 7/2004 | Barmore ................. B32B 27/08 428/34.2 |
| 2010/0140502 A1* | 6/2010 | Guckian ................. C09D 11/38 250/459.1 |
| 2010/0143675 A1 | 6/2010 | Guckian et al. |

FOREIGN PATENT DOCUMENTS

WO    WO 2007/120637    10/2007

OTHER PUBLICATIONS

International Search Report for PCT/NL2016/050037, dated Jun. 14, 2016, 4 pages.
Written Opinion of the ISA for PCT/NL2016/050037, dated Jun. 14, 2016, 9 pages.
McEvoy et al, "*Optical sensors for application in intelligent food packaging technology*", Proceedings of SPIE, SPIE, International Society of Optical Engineering, vol. 4876, No. 2, pp. 806-815.
JP Application No. 2017-556507, Notice of Reasons for Refusal dated Jul. 30, 2018.

* cited by examiner

*Primary Examiner* — Ling Siu Choi
*Assistant Examiner* — Ronald Grinsted
(74) *Attorney, Agent, or Firm* — Nixon & Vanderhye P.C.

(57) ABSTRACT

The invention relates to a multi-layered packaging foil comprising a layer L-1 having an oxygen gas transmission rate OGTR-1; a luminescent compound having the property that its luminescence is capable of being quenched by oxygen; and a layer L-2 adhering to L-1 and to the luminescent compound. The layer L-2 has an oxygen gas transmission rate OGTR-2 that is at least 20 times higher than OGTR-1, and the luminescent compound is present between L-1 and L-2. The invention further relates to a packaging comprising a packaging foil of the invention and to a method for measuring the oxygen content in a packaging.

15 Claims, 2 Drawing Sheets

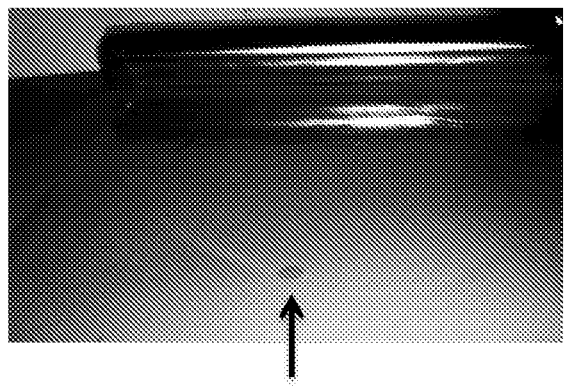
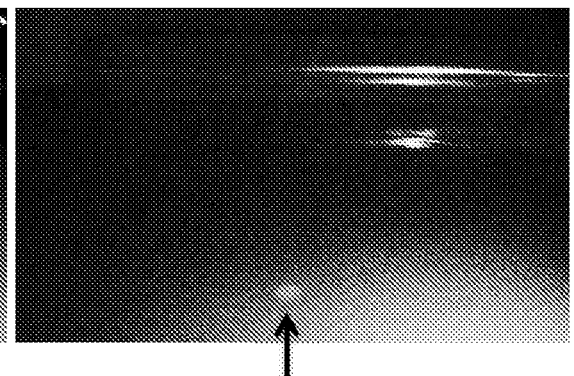
FIG. 1A          FIG. 1B
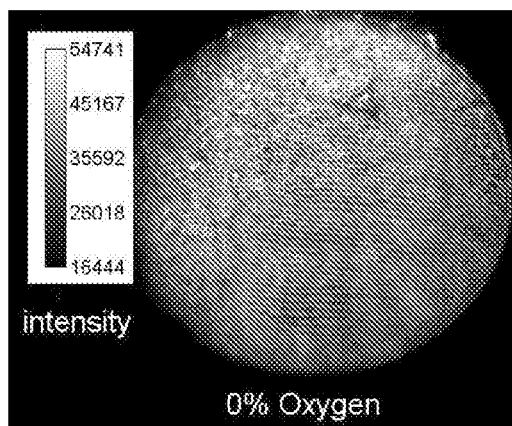
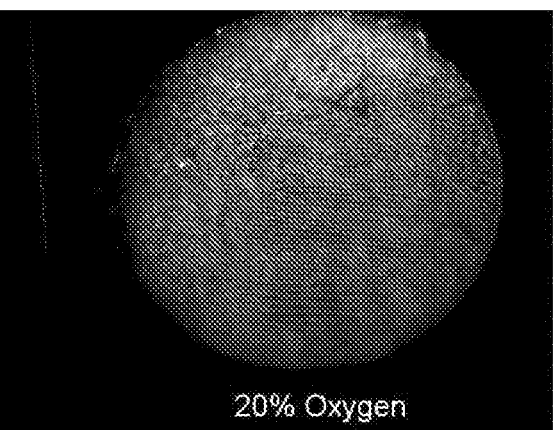
FIG. 2A          FIG. 2B

PACKAGING FOIL COMPRISING A LUMINESCENT COMPOUND

CROSS-REFERENCE TO RELATED APPLICATIONS

This application is the U.S. national phase of International Application No. PCT/NL2016/050037 filed 16 Jan. 2016, which designated the U.S. and claims priority to NL Patent Application No. 2014149 filed 16 Jan. 2015, the entire contents of each of which are hereby incorporated by reference.

FIELD

The invention relates to a multi-layered packaging foil, to a method for producing such foil, to a packaging comprising such foil and to a method for measuring the oxygen content in such packaging.

BACKGROUND SUMMARY

Many products are packed under a protective atmosphere, which method is commonly known as modified atmosphere packaging (MAP). It is in particular applied for food products such as meat, fish, fruit, vegetables, instant meals, pastry, or potato crisps. Other products that may be MAP-packed are cosmetics, medicaments, chemicals and sterile objects such as medical or laboratory instruments (e.g. needles, syringes, bandages). Often, the applied modified atmospheres have a reduced oxygen content and an increased nitrogen and/or carbon dioxide content. However, in certain cases, an atmosphere rich in oxygen is used.

On the way to the consumer, the protective atmosphere of a MAP-package can be impaired at many stages. The package can for example be damaged by inappropriate handling during production, transport or placement in a store or working space, thereby creating an open connection with the outside environment. Also, mistakes can be made during the process of packaging, for example the package may be inadequately sealed or the gas that is used for creating the protective atmosphere is of the wrong composition. As a result, large amounts of (food) products become unsuitable for use or consumption and need to be disposed, for example by the manufacturer/packager, carrier, store, hospital, laboratory or end-user. In addition, there is a waste of packaging material.

By measuring the composition of the atmosphere in a MAP-package, it is possible to identify MAP-packages that are not suitable for use by the end-user. Preferably, this is performed at an early stage, for example already at the production/packaging line. Conventional measuring methods are often invasive, i.e. the atmosphere is permanently impaired after the measurement and the product is not suitable anymore for the intended use. In addition, such measurements are usually made on a random sample representing an entire batch. As a result, an entire batch can be rejected on the basis of one sample. Conversely, it is possible that improperly packed articles inadvertently pass a quality control and find their destiny at the end-user. A so-called "100% check" with a non-invasive method would therefore be desired. This would not only be useful at the production/packaging line, but also for the end-user. It can offer the certainty that the product he/she is intended to buy or use is indeed still in a protective atmosphere. However, it is usually too complicated and too expensive to test each and every package, because this requires that means for sensing oxygen are included in every MAP-package.

Providing every MAP-package with sensing means is conventionally done for example by using an unlaminated patch that can measure the inner atmosphere, which patch is glued to the inside of the foil. Placing and gluing such patches is costly, time-consuming and difficult to integrate in current processes for making foils and MAP-packages. Moreover, there is a risk that patches come loose from the foil and get in direct contact with the product. Thus far, unlaminated patches seem only to be used for research purposes and product development.

A packaging foil with an attached oxygen sensor is known from, for example, WO2007120637 A2. This publication describes a food packaging membrane for a sealable package, comprising a luminescence indicator capable of detecting one or more analytes within the package contacting the membrane. The detection is performed with a sensor comprising a ruthenium-based luminescence compound dispersed within a diffusible polymer matrix. A disadvantage of such membrane is that the sensor needs to be in fluid communication with the package interior and the contents of the package, i.e. that a gas flow is required between the main headspace of the packaging and the sensor material. In this way, the sensor may come into direct physical contact with the contents of the packaging and thereby contaminate such contents. This is undesired, in particular when the contents are edible products. Another disadvantage is that the matrix with the luminescence compound has to meet the requirements of high structural integrity (i.e. it is not subject to distortion or abrasion by physical contact with the contents of the package) and strong adhesion (i.e. it is not wiped away from the surface by physical contact with the contents of the package.

It is therefore an objective of the invention to provide a packaging foil with oxygen sensing means that can be used to prepare a MAP-packaging wherein the presence of oxygen in the atmosphere of the packaging can be determined in a non-invasive manner. In particular, it is aimed that it can be determined whether the amount of oxygen lies above a certain level, or that the presence of oxygen is determined in a quantitative way.

It is also an objective to provide a packaging foil with oxygen sensing means that can be introduced in a conventional process for packaging articles wherein each produced packaging contains the oxygen sensing means.

It is also an objective of the invention to provide a packaging comprising an object enclosed by the packaging and comprising oxygen sensing means that can measure the oxygen in the atmosphere surrounding the object, wherein the oxygen sensing means cannot come into physical contact with the object present in the packaging.

It has now been found that one or more of these objectives can be reached by using a particular combination of foils and a luminescent dye in a particular arrangement.

Accordingly, the present invention relates to a multi-layered packaging foil comprising
 a layer L-1 having an oxygen gas transmission rate OGTR-1;
 a luminescent compound having the property that its luminescence is capable of being quenched by oxygen;
 a layer L-2 adhering to L-1 and to the luminescent compound, the layer L-2 having an oxygen gas transmission rate OGTR-2 that is at least 20 times higher than OGTR-1;
wherein the luminescent compound is present between L-1 and L-2.

BRIEF DESCRIPTIONS OF THE DRAWINGS

FIGS. 1A and 1B are photographs of the foil of the invention, each taken from the foil roll shown in the background wherein FIG. 1A is taken under normal conditions (ambient light), and FIG 1B is taken while the foil is illuminated by UV-light;

FIGS. 2A and 2B show the luminescence of the sensor spot in the roil at 0% of oxygen (FIG. 2A) and at 20% of oxygen (FIG. 2B);

DETAILED DESCRIPTION

Figure 3:
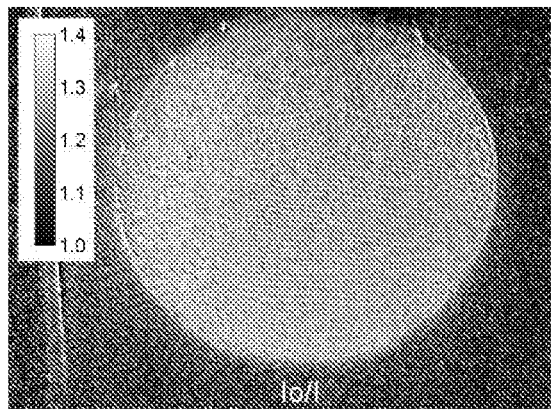
FIG. 3 is a photograph which displays the ratio $I_0/I$ over the entire sensor spot.

The layer L-1 of a packaging foil of the invention serves as an oxygen barrier layer. When a packaging foil of the invention is present as a sealing layer on a container and forming a MAP package, it is L-1 that prevents oxygen from transmitting into the container (together with the walls of the container).

To achieve the barrier properties suitable for a MAP package, the oxygen gas transmission rate OGTR-1 is usually 100 $cm^3$ $m^{-2}$ $day^{-1}$ or less, 75 $cm^3$ $m^{-2}$ $day^{-1}$ or less, 50 $cm^3$ $m^{-2}$ $day^{-1}$ or less, or 25 $cm^3$ $m^{-2}$ $day^{-1}$ or less. Preferably, it is 10 $cm^3$ $m^{-2}$ $day^{-1}$ or less, more preferably it is 5 $cm^3$ $m^{-2}$ $day^{-1}$ or less, and even more preferably it is 1 $cm^3$ $m^{-2}$ $day^{-1}$ or less.

The oxygen gas transmission rate OGTR-2 is usually 500 $cm^3$ $m^{-2}$ $day^{-1}$ or more, 1,000 $cm^3$ $m^{-2}$ $day^{-1}$ or more, 2,000 $cm^3$ $m^{-2}$ $day^{-1}$ or more, or 5,000 $cm^3$ $m^{-2}$ $day^{-1}$ or more. Preferably, it is 10,000 $cm^3$ $m^{-2}$ $day^{-1}$ or more, more preferably it is 20,000 $cm^3$ $m^{-2}$ $day^{-1}$ or more, and even more preferably it is 50,000 $cm^3$ $m^{-2}$ $day^{-1}$ or more.

In an embodiment, OGTR-1 is 50 $cm^3$ $m^{-2}$ $day^{-1}$ or less at 25° C. and 0% RH at 1 atm oxygen partial pressure difference (ASTM D3985), and OGTR-2 is at least 50,000 $cm^3$ $m^{-2}$ $day^{-1}$ at 25° C. and 0% RH at 1 atm oxygen partial pressure difference (ASTM D3985).

For the purpose of the invention, OGTR's are determined according to the standard test method ASTM D3985. The OGTR's are determined at 25° C. and 0% RH at 1 atmosphere partial pressure difference across the foil without a substantial difference in total pressure across the foil.

The luminescent compound may in principle be any luminescent compound, as long as it has the property that its luminescence is capable of being quenched by oxygen. It is for example a porphyrin, i.e. a compound comprising a porphyrin moiety or a substituted porphyrin moiety. The luminescent compound is for example selected from the group of platinum(II)-meso-tetra(pentafluorophenyl) porphine (Pt-TFPP), palladium coproporphyrin (PdCPP), platinum or palladium octaethylporphyrin (PtOEP,PdOEP), platinum or palladium tetraphenylporphyrin (PtTPP, PdTPP), ruthenium(II)-tris-4,7-diphenyl-1,10 phenantroline (Ru-DPP), iridium(III) acetylacetonato-bis(3-(benzothiazol-2-yl)-7-(diethylamino)-coumarin), camphorquinone and erythrosin B.

The luminescent compound is the sensing compound on which the sensoric action of a foil of the invention relies. Since oxygen is capable of quenching the luminescence, the luminescence intensity and/or the luminescence lifetime are a measure of the amount of oxygen present.

Since layer L-2 adheres to L-1 as well as to the luminescent compound, it follows that the luminescent compound (or its combination with an eventual matrix material) occupies a surface area that is smaller than the adjacent surface areas of L-1 and L-2 (i.e. the surface areas of L-1 and L-2 that are facing each other after laminating one on the other). On the adjacent surface areas where the luminescent compound is not provided, L-1 and L-2 adhere to each other. On the other hand, on the surface area where the luminescent compound is indeed provided, L-1 and L-2 do not adhere to each other but to the surface of the luminescent compound (or to its combination with an eventual matrix material).

It is important that the luminescent compound is completely enclosed by L-1 and L-2. This means that along all the edges of the shape of the luminescent compound, L-1 and L-2 adhere to each other. This ensures that there is no direct contact of the luminescent compound with an outside atmosphere. There may for example not be a channel between L-1 and L-2 that allows transport of gas directly to the luminescent compound. Neither may the foil be structured such that an edge of the shape of the luminescent compound coincides with an edge of L-1 and/or L-2, so that a cross-section of the shape is in direct contact with an outside atmosphere. In other words, the luminescent compound is completely sealed by L-1 and L-2.

The luminescent compound may in principle be present in any shape. Usually, however, it is of a flat shape, i.e. it has one dimension that is substantially smaller than each of the other two dimensions. For example, the smallest dimension is at least 50 times, at least 100 times, at least 200 times, at least 500 times, at least 1,000 times, at least 2,000 times, at least 5,000 times or at least 10,000 times smaller than any of the other two dimensions. The thickness is usually less than 100 μm, for example in the range of 0.1-50 μm, in particular in the range of 0.5-10 μm. The length and the width may independently of each other be 1 mm or more, 2 mm or more, 5 mm or more or 10 mm or more.

The luminescent compound may be present as a spot, in particular looking like a two-dimensional round figure (i.e. a circle) or a non-circular two-dimensional figure (e.g. an elliptic figure) wherein the length of the smallest dimension is for example less than two times the length of the largest dimension.

The relationship between the luminescence intensities and lifetimes in the absence ($I_0$, $tau_0$ ($\tau_0$), respectively) and presence (I, tau ($\tau$), respectively) of oxygen is described by the Stern-Volmer equation (I):

$$I_0/I = tau_0/tau = 1 + K_{SV} pO_2 \tag{I}$$

where $pO_2$ is the partial pressure of oxygen in the medium being sensed and $K_{SV}$ is the Stern-Volmer quenching constant. Relative luminescence intensities ($I_0/I$) or relative luminescence lifetimes ($tau_0/tau$) can be measured experimentally. Ideally, a plot of ($I_0/I$) or ($tau_0/tau$) against $pO_2$ gives a straight line with a slope of $K_{SV}$ and an intercept of unity. A calibration curve can be made of intensity or lifetime versus concentration, and from this the concentration of the oxygen in the medium can be determined.

A deviation from the ideal case of the Stern-Volmer equation may be described by the following adapted Stern-Volmer equation (II):

$$\frac{I}{I_0} = \frac{\tau}{\tau_0} = \frac{1-\alpha}{1+K_{SV}C} + \alpha \tag{II}$$

This equation accounts for a non-quenchable fraction alpha (a) within the sensor. Such fraction alpha is usually at least 4% of the total, but may become substantial when the luminescent compound is present in a form that cannot be quenched and/or in a form that is not sufficiently accessible to oxygen.

By definition, the fracture $I_0/I$ or $tau_0/tau$ is at least 1 (i.e. $I_0=I$ or $tau_0=tau$). This is in the case wherein the medium to be sensed is void of oxygen. The fracture is largest when the oxygen content in the medium being sensed is at a maximal value (i.e. I or tau, respectively, is at a minimal value). Such value usually corresponds to the oxygen content in air (20.85 mol %) or to 100% oxygen, in which case I is defined as $I=I_{atm}$ and $I=I_{100\% \ O2}$, respectively. The minimal and maximal values of the fracture $I_0/I$ and $tau_0/tau$ define the two end-points of the measuring range for the luminescence quenching. The larger the range, the lower is the signal to noise ratio and the more accurate is the measurement. It is therefore preferred that the range (and thus the fracture $I_0/I$ or $tau_0/tau$) is as large as possible.

The fracture $I_0/I$ or $tau_0/tau$ is usually at least 1.20, at least 1.30, at least 1.50 or at least 2.0. Preferably, it is 2.5 or more, 3.0 or more or 3.5 or more. More preferably, it is 4.0 or more and even more preferably it is 5 or more.

The luminescent compound is in principle present as such, but it is also possible that it is contained in a matrix material. Thus, a matrix material comprising the luminescent compound may be present between L-1 and L-2. In the art, a matrix material provides structural integrity to the luminescent compound and offers a good adherence to the foil. For the present invention, structural integrity and good adherence are a minor issue, since the luminescent compound is enclosed by the two layers, fixing its position and its shape. Therefore, a matrix material is in principle not necessary for a foil of the invention.

A matrix material preferably has an open structure and/or has pores, so that oxygen transport through the material is possible. In this way, there is sufficient access of oxygen to the luminescent compound, so that oxygen can easily reach and quench the luminescent dye. A high accessibility results in a low value of the non-quenchable fraction alpha as defined in the adapted Stern-Volmer equation (II), which improves the accuracy of the sensor. The skilled person preparing a particular packaging foil with a particular sensor can judge on the necessity of a matrix.

A matrix material may also be advantageous during the process for preparing a multi-layered packaging foil of the invention, in particular during the application of the luminescent compound. The matrix material may assist in 1) applying the luminescent compound in a stable (and therefore reproducible) shape; 2) applying the luminescent compound in a well-defined (and therefore reproducible) quantity; and 3) preventing disruption or detachment of the applied luminescent compound during the period of the manufacturing process between applying the luminescent compound on a first layer and laminating it by a second layer (for example when the luminescent compound is not directly laminated).

If present, the matrix material comprises for example a material selected from the group of polystyrene, silicone gels, nitrocellulose and cellulose acetate butyrate. The matrix material with the luminescent compound therein may be prepared by dissolving the luminescent compound in a solution of the matrix material (typically an ink or a varnish), followed by drying the solution. Upon drying, the solution (for example the applied ink or varnish that contains the luminescent compound) forms a porous matrix material comprising the luminescent compound.

The oxygen quenching properties of the matrix material with the luminescent compound therein may be improved by the presence of a plasticizer, preventing dye aggregation and increasing the oxygen permeability in the polymer matrix.

It is preferred that L-1 is transparent for the radiation used for excitation as well as for the radiation of the luminescent light. It is also preferred that the matrix, if present, is transparent for the radiation used for excitation as well as for the radiation of the luminescent light. This is because the excitation of the luminescent compound usually occurs from the outside of the package, just as the detection of the resulting luminescent light. Transparency improves the transmission of the radiation through the material.

The layer L-2 of a packaging foil of the invention serves to protect the luminescent compound and/or the matrix in which the luminescent compound is present. In addition, it fixes its shape and position and prevents migration of the dye over the surface of the foil and further into the container in the event that the foil is used to seal a container. Since L-2 is between the sensor and the headspace containing the atmosphere to be measured, it is essential that oxygen can penetrate through L-2 at a sufficient rate. This rate is preferably defined with reference to the rate at which oxygen can penetrate through L-1. In a packaging foil of the invention, the oxygen transmission rate of L-2 (i.e. OGTR-2) is at least 20 times higher than the oxygen transmission rate of L-1 (i.e. OGTR-1). In this way, the influence of the penetration of atmospheric oxygen through L-1 onto the luminescent compound is small in comparison with the penetration of headspace oxygen through L-2 onto the luminescent compound. OGTR-2 may also be 50 times higher or 75 times higher than OGTR-1. Preferably, it is at least 100 times higher than OGTR-1. For example, it is at least 200 times higher, at least 500 times higher, at least 750 times higher, at least 1,000 times higher, at least 2,000 times higher, at least 5,000 times higher, at least 10,000 times higher, at least 20,000 times higher or at least 50,000 times higher.

In practice however, a particular minimal value of OGTR-2 may be preferred so as to have a suitable response time of the sensor. This is because a lower OGTR-2 value would increase the time wherein oxygen reaches the luminescent compound and thus increase the response time of the sensor, which may be undesired. Layer L-2 may therefore have a OGTR-2 of $1.0 \times 10^4$ $cm^3$ $m^{-2}$ $day^{-1}$ or more, $5.0 \times 10^4$ $cm^3$ $m^{-2}$ $day^{-1}$ or more, $1.0 \times 10^5$ $cm^3$ $m^{-2}$ $day^{-1}$ or more, $5.0 \times 10^5$ $cm^3$ $m^{-2}$ $day^{-1}$ or more or $1.0 \times 10^6$ $cm^3$ $m^{-2}$ $day^{-1}$ or more.

In principle, L-1 and L-2 may have, independently of each other, any thickness that is suitable for the particular application of the packaging foil. Usually, however, the thickness of L-1 and L-2 is, independently of each other, 250 μm or less. It may also be 200 μm or less, 150 μm or less or 125 μm or less. In particular, it is 100 μm or less, 90 μm or less, 75 μm or less, 50 μm or less, 35 μm or less or 25 μm or less. The thickness of L-1 and L-2 may be, independently of each other, 1 μm or more or 2 μm or more. Usually, it is 5 μm or more or 10 μm or more. In particular, it is 15 μm or more, 20 μm or more, 30 μm or more or 45 μm or more. The thickness of L-1 and L-2 may be, independently of each other, in the range of 3-160 μm, in particular it is in the range of 6-120 μm, more in particular it is in the range of 12-80 μm and even more in particular it is in the range of 18-60 μm or in the range of 24-40 μm.

In particular, the invention relates to a multi-layered packaging foil comprising a layer L-1 having an oxygen gas transmission rate OGTR-1 of 10 cm$^3$ m$^{-2}$ day$^{-1}$ at 25° C. and 0% RH at 1 atm oxygen partial pressure difference (ASTM D3985) or less;

a luminescent compound having the property that its luminescence is capable of being quenched by oxygen;

a layer L-2 adhering to L-1 and to the luminescent compound, the layer L-2 having an oxygen gas transmission rate OGTR-2 that is at least 500 cm$^3$ m$^{-2}$ day$^{-1}$ at 25° C. and 0% RH at 1 atm oxygen partial pressure difference (ASTM D3985) or more;

wherein the luminescent compound is present between L-1 and L-2.

In particular, OGTR-1 is 5 cm$^3$ m$^{-2}$ day$^{-1}$ or less, and OGTR-2 is 1,000 cm$^3$ m$^{-2}$ day$^{-1}$ or more. More in particular, OGTR-1 is 3 cm$^3$ m$^{-2}$ day$^{-1}$ or less, and OGTR-2 is 3,000 cm$^3$ m$^{-2}$ day$^{-1}$ or more. Even more in particular, OGTR-1 is 1 cm$^3$ m$^{-2}$ day$^{-1}$ or less and OGTR-2 is 10,000 cm$^3$ m$^{-2}$ day$^{-1}$ or more.

An advantage of the present invention is that the luminescent compound (or the matrix in which it is present) does not have to meet the stringent requirements of those mentioned in the art, such as a high structural integrity and strong adhesion. This is because the luminescent compound (or the matrix in which it is dispersed) is covered with L-2. This layer offers protection, in particular against physical contact of the contents of the package, and ensures that the luminescent compound (or the matrix in which it is dispersed) stays in place, i.e. does not detach from or move over the surface of L-1.

As mentioned above, a decreased diffusion of oxygen to the luminescent compound may lead to an increase of the non-quenchable fraction alpha and an increased response time. It was therefore contemplated that the presence of a layer that is placed on top of the luminescent compound would also hinder the diffusion of oxygen and so result in an undesirably high non-quenchable fraction alpha and/or an undesirably long response time.

Surprisingly, however, it was found that the presence of a layer permeable to oxygen still results in fractures of $I_0/I$ or $tau_0/tau$ that define a suitable measuring range for the luminescence quenching. The oxygen radicals that are formed appear to fall back in their ground state within a second (likely within 10, 20 or 30 ms). It will therefore be unlikely that oxygen radicals diffuse out of the matrix (if present), and even more unlikely that they diffuse through the layer L-2 into the headspace of the product. The radicals will therefore not have an effect on the integrity of the packed product. The sensor does not appear to consume oxygen molecules and oxygen radicals.

The layers L-1 and/or L-2 are usually present as a composition of a plurality of layers, in which composition neighboring layers adhere to each other. The layer L-1 may comprise a layer of a polymer selected from the group of low-density polyethylene, linear low-density polyethylene, high-density polyethylene, polypropylene, biaxially oriented polypropylene, poly(ethylene-vinyl acetate), poly(ethylene-vinyl alcohol), poly(ethylene-acrylic acid), polystyrene, poly(styrene-1,3-butadiene), oriented polystyrene, poly(vinyl alcohol), poly(vinyl chloride), poly(vinylidene chloride), poly(tetrafluoroethylene), poly(ethylene terephthalate), poly(ethylene naphthalate), polycarbonates, polyamides (in particular oriented polyamides) such as nylon-MXD6, polyacrylonitrile, regenerated cellulose and poly(lactic acid).

In case L-1 is composed of a plurality of layers, it is usually one particular layer that provides L-1 with the high barrier function. Such layer is for example selected from the group of high-barrier polymers, metals, inorganic oxides such as silica or alumina, and carbon in graphitic or diamond form. High barrier polymers may be readily selected by the man skilled in the art from their reported permeabilities.

Usually, L-1 comprises in addition to the oxygen barrier layer, one or more other layers that fulfill other functions such as providing more strength to L-1. Such other layers often have a higher oxygen gas transmission rate than the oxygen barrier layer. In some embodiments, such other layer is in direct contact with the luminescent compound. This is especially the case when the luminescent compound is first laminated between L-2 and one of the other layers of L-1 (i.e. other layers than the oxygen barrier layer of L-1) so that an intermediate foil is formed wherein the luminescent compound is already enclosed between two layers (sealed) but wherein the oxygen barrier layer is not yet present (i.e. the layer on one side of the luminescent compound is L-2, but the layer on the other side is not yet complete since it does not yet have OGTR-1). The advantage of this design is that a sticker comprising the luminescent compound can be prepared, which can be mounted on a foil having an OGTR-1 in a second step. Upon placing the sticker, a foil of the invention is formed since the luminescent compound is then present between a layer with OGTR-1 and a layer with OGTR-2. The method for preparing such foil of the invention is further elaborated hereinbelow.

The layer L-2 may comprise a layer of a polymer selected from the group of polyethylene, polypropylene, PP compound, poly(ethylene-terephthalate) and oriented polyamide.

If necessary, a glue is present in a packaging foil of the invention, in particular for improving the adherence of L-1 and L-2 to each other and/or to the luminescent compound. When a glue is present between both layers, the glue may be part of L-1 or L-2, depending on the location of the luminescent compound (for example, when glue is present between L-2 and the luminescent compound, it is understood to be part of L-2). Preferably, a possible glue is part of L-1, and not of L-2, so that it does not influence OGTR-2. For this reason, it is preferred that a foil of the invention is prepared by printing the luminescent compound directly on L-2, followed by the application of an eventual glue and the lamination with L-1 (which process is further elaborated hereinbelow). This order of steps has the effect that there is no glue between the luminescent compound and L-2.

The invention further relates to a packaging comprising a packaging foil of the invention.

A multi-layered packaging foil according to the invention is usually prepared by the step-wise application of the different layers and the luminescent compound in a particular order. In principle, two different methods exist for such method. In the first method, the foil is built up starting with L-1. In the second method, the order is reversed. This means that the build-up of the foil starts with L-2.

Accordingly, the invention further relates to a method for preparing a multi-layered packaging foil, comprising providing a layer L-1 having an oxygen gas transmission rate OGTR-1; then applying on a part of the surface of L-1 a luminescent compound having the property that oxygen quenches the luminescence; then laminating L-1 with a layer L-2 having an oxygen gas transmission rate OGTR-2 that is at least 20 times higher than OGTR-1, wherein L-2 completely covers the applied luminescent compound.

Alternatively, the invention relates to a method for preparing a multi-layered packaging foil, comprising
- providing a layer L-2 having an oxygen gas transmission rate OGTR-2; then
- applying on a part of the surface of L-2 a luminescent compound having the property that oxygen quenches the luminescence; then
- laminating L-2 with a layer L-1 having an oxygen gas transmission rate OGTR-1 that is at least 20 times lower than OGTR-2, wherein L-1 completely covers the applied luminescent compound.

In the above method, first the luminescent compound is provided on L-2, and then L-1 is provided. There exists a variation of this method wherein L-1 is provided in two steps. This allows the preparation of the intermediate foil as is also mentioned above. In such foil, the luminescent compound is already enclosed between two layers (sealed), but the foil does not yet contain the oxygen barrier layer. In this way, a sticker comprising the luminescent compound can be prepared, which can be mounted on a foil having an OGTR-1. Upon placing the sticker, a foil of the invention is formed.

Accordingly, the invention further relates to a method for preparing a multi-layered packaging foil, comprising
- providing a layer L-2 having an oxygen gas transmission rate OGTR-2; then
- applying on a part of the surface of L-2 a luminescent compound having the property that oxygen quenches the luminescence; then
- laminating L-2 with a first layer of a material to produce an intermediate foil, wherein the first layer completely covers the applied luminescent compound; then
- applying a second layer on the first layer of the intermediate foil, wherein the second layer has an oxygen gas transmission rate OGTR-1 that is at least 20 times lower than OGTR-2, and wherein the second layer completely covers the first layer;

The intermediate foil does not need to be provided with the second layer immediately after it has been prepared, but it may be prepared as such, and may then also be sold, shipped, and stored as such. It can for example be provided with a sticking layer and optionally with a protective sheet to protect the sticking layer. In this way, a sticker is formed that can be applied on a packaging foil having the oxygen barrier layer so that a foil of the invention is prepared, for example in a (roll-to-roll) production process of a packaging foil, or in a packaging process wherein such foil is used to seal a package.

The OGTR of a layer L-1 and of a layer L-2 remains substantially the same during its processing in a method of the invention. In this way, a multi-layered packaging foil according to the invention can be prepared by selecting a starting material for each layer that has the OGTR that is desired in the final foil.

In a method of the invention, OGTR-2 may also be 50 times or 75 times higher than OGTR-1. Preferably, it is at least 100 times higher than OGTR-1. For example, it is at least 200 times higher, at least 500 times higher, at least 750 times higher, at least 1,000 times higher, at least 2,000 times higher, at least 5,000 times higher, at least 10,000 times higher, at least 20,000 times higher or at least 50,000 times higher.

For applying the luminescent compound, a method of the invention may make use of a conventional printing technique, in particular of flexoprinting or continuous inkjet printing. These printing techniques are able to print inks on foils in well-defined shapes and/or in reproducible quantities. Moreover, such printing may be performed at conditions that are comparable to those of conventional printed foil production processes (e.g. at production speeds of up to 400 m/min). The ink that is applied by these techniques comprises the luminescent compound. To this end, the luminescent compound, and an eventual matrix material, may be dissolved in a solvent. Preferably, the solvent is evaporated prior to the laminating step.

Printing has the advantage that high turnovers can be achieved. It is however not necessary to apply the luminescent compound by printing. It is also possible to apply a solution of the luminescent compound and eventually the ink in a manual way, e.g. by pipetting.

The invention further relates to a multi-layered packaging foil obtainable by a method of the invention.

The invention further relates to a method for measuring the oxygen content in a packaging comprising a packaging foil according to the invention, comprising
- illuminating the luminescent compound present in the foil of the packaging with electromagnetic radiation of a wavelength at which luminescence occurs; then
- measuring the intensity or the lifetime of the luminescence of the luminescent compound present in the foil; then
- identifying which concentration of oxygen corresponds to the measured lifetime or intensity, by making use of the Stern-Volmer relationship of the particular foil that is used in the packaging.

By the Stern-Volmer relationship is meant the graph representing $I_0/I$ or $tau_0/tau$ as a function of the oxygen concentration (% oxygen in the gas phase) according to the Stern-Volmer equation (I) or the adapted Stern-Volmer equation (II).

The present invention is not only suitable for measuring the oxygen content in a packaging. It is also possible to measure other gaseous analytes such as ammonia or carbon dioxide. Accordingly, the present invention further relates to a multi-layered packaging foil comprising
- a layer L-1 having an gaseous analyte transmission rate GATR-1;
- a luminescent compound having the property that its luminescence is capable of being quenched by the gaseous analyte;
- a layer L-2 adhering to L-1 and to the luminescent compound, the layer L-2 having a gaseous analyte transmission rate GATR-2 that is at least 20 times higher than GATR-1;

wherein the luminescent compound is present between L-1 and L-2.

In a foil of the invention, the gaseous analyte may be selected from the group of ammonia ($NH_3$), carbon dioxide ($CO_2$), water ($H_2O$), hydrogensulfide ($H_2S$) and amines, such as trimethylamine ($NMe_3$) or triethylamine ($NEt_3$).

The detailed description of such packaging foil that is suitable for measuring for these and other gaseous analytes is analogous to the description hereinabove directed to a packaging foil that is suitable for measuring oxygen. The term GATR, for example, corresponds to the term OGTR.

EXAMPLES

Preparation of the Foils

Two kilometers of foil having spots of luminescent compound were produced by making use of the technique of flexoprinting. The spots were printed as a circular shape with the dye dissolved in a UN1213 printing ink based on a technical printing varnish on a layer L-2 at a speed of 40 m/min. The ink was obtained from Sun Chemical, comprising (1) technical printing varnish of Sunprop Line 00LSF01, (2) Extender NC Flexo NC of 10LZD-05 and (3) adhesion promoter of 10-ZH-08. This layer L-2 comprised a polyethylene layer and a polypropylene layer, had a 37 µm thickness and an oxygen gas transmission rate (OGTR-2) of 3,000 cm$^3$ m$^{-2}$ day$^{-1}$ at 25° C. and 0% RH at 1 atm oxygen partial pressure difference (ASTM D3985). The diameter of the spots is 1 cm. The concentration of the oxygen sensing dye (Pt(II)meso-tetra(pentafluorophenyl)porphine, Frontier Scientific) in the printing ink is 2 g/l. One spot required approximately 0.2 µl of ink. Subsequently (and after drying of the ink), a layer L-1 was laminated on the layer L-2 comprising the spot. The layer L-1 comprised a polyester layer with a silica coating, had a 12 µm thickness and an oxygen gas transmission rate (OGTR-1) of <1 cm$^3$ m$^{-2}$ day$^{-1}$ at 25° C. and 0% RH at 1 atm oxygen partial pressure difference (ASTM D3985).

Characterization of the Foils

The obtained foil was transparent and had mechanical properties similar to known packaging foils. The spots enclosed in the foil retained their shape upon handling of the foil and could not be dislocated by passing an object over the surface of the foil (it could for example not be wiped away or deformed by brushing with a finger). FIGS. 1A and 1B are two photographs of the foil of the invention, each taken from the foil roll shown in the background. The photograph of FIG. 1A is taken under normal conditions (ambient light), demonstrating a spot that is darker than the foil (the spot is indicated with the vertical arrow). The photograph of FIG. 1B is taken while the foil is illuminated by UV-light, while only the red channel is used for displaying the picture in black and white. The photograph of FIG. 1B displays a spot that is brighter than the foil (the spot is indicated with the vertical arrow).

The luminescence intensity of the sensor spot in the foil was measured under different oxygen atmospheres with a black and white 16 bit camera (Basler industrial vision) with a bandpass filter (665 nm±25 nm) mounted on the lens. The luminescence intensity was measured when the foil was exposed to a (gaseous) environment containing 0% of oxygen ($I_0$), and when it was exposed to 20% of oxygen (I). FIGS. 2A and 2B are photographs showing the luminescence at 0% of oxygen (FIG. 2A) and at 20% of oxygen (FIG. 2B). The images of FIG. 2A and 2B demonstrate that the luminescence intensity changed due to the variation of the oxygen concentration.

From both of the images of FIGS. 2A and 2B it is possible to calculate the ratio $I_0/I$. FIG. 3 is a photograph which displays the ratio $I_0/I$ over the entire spot (the diagram legend on the left FIG. 3 shows the correlation of the ratio $I_0/I$ with the shades of grey in the spot). The average ratio of the spot in FIG. 3 appears to be 1.28.

For comparison, a couple of meters of the printed L-2 foil (i.e. L-2 foil provided with the luminescent compound) was not laminated with L-1. The non-laminated foil was put in a gas-tight container in which the gas (in particular oxygen) concentration could be changed. Accordingly, this foil had the luminescent compound in fluid communication with the atmosphere in the container. This provides a configuration wherein the lack of layer L-2 is mimicked, i.e. a packaging foil of the prior art. Luminescence measurements performed on this foil offer comparative data. This foil will be referred to by the term "non-coated". A foil of the invention (which includes the layer L-2 as well as the layer L-1, with the luminescent compound therein between) will be referred to by the term "coated".

Measuring the Oxygen Content in a MAP-Packaging

A MAP-packaging was prepared by sealing a container with a foil of the invention ("coated"). For comparison, a second MAP-packaging was prepared with a foil lacking the layer L-1 ("non-coated"). The containers had a gastight connection that allowed changing the gas concentration in the container. A series of nine oxygen concentrations was flushed continuously at 4 L h$^{-1}$ through the containers fully replacing the headspace within 10 seconds. The gas mixtures were made by electronic mass flow controllers (Brooks Instruments) with an accuracy of 0.05% of the max flow rate of the mass flow controller. Measurement of the luminescence lifetime or intensity was determined after the spot reached steady state values.

Figure 4:
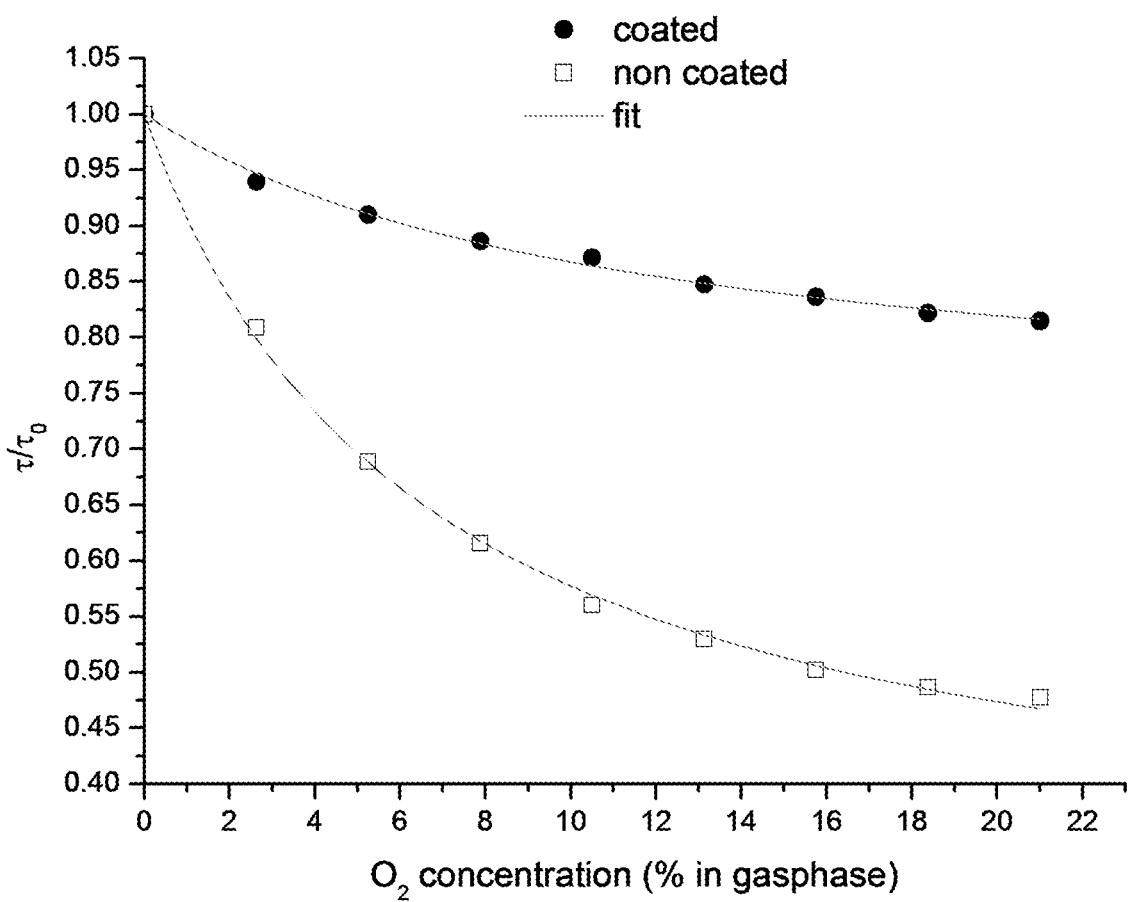
FIG. 4 is a Stern-Volmer plot of the ratio $tau_0/tau$ versus $O_2$ concentrations of coated and uncoated foils.

With the obtained data, a Stern-Volmer plot could be made for the two foils used for the MAP-packagings. The plots are fit with the adapted Stern-Volmer equation (II) and are shown in FIG. 4. In Table 1, for each of the two foils the following quantities are given: (1) the non-quenchable fraction alpha with its standard error, (2) the Stern-Volmer quenching constant, (3) the fit quality of the plot, (4) the ratio $tau_0/tau$ and (5) the luminescence lifetimes under an anaerobic environment (100% $N_2$) and under atmospheric environment (21% $O_2$).

TABLE 1

| | Fit with adapted Stern-Volmer equation (II) | | | | | | | |
|---|---|---|---|---|---|---|---|---|
| | | Standard error of | | Standard error of | Fit quality | $tau_0/$ | lifetime (µs) | |
| | α | α | $K_{sv}$ | $K_{sv}$ | ($r^2$) | tau | 0% $O_2$ | 21% $O_2$ |
| Coated | 0.71608 | 0.0139 | 0.08731 | 0.00923 | 0.99497 | 1.20 | 66 | 55 |
| Non-coated | 0.30266 | 0.01253 | 0.15402 | 0.00784 | 0.99854 | 2.13 | 66 | 31 |

The data obtained with both foils show the effect of lamination (to thereby cover the luminescent compound) on the characteristics of the luminescent compound (as compared to known foils wherein the luminescent compound remains uncovered). When the luminescent compound is laminated (i.e. the luminescent compound is present between L-1 and L-2), then the result is in an increase of a, a decrease of $K_{sv}$ and a decrease of the ratio $tau_0/tau$. The overall effect is that the sensor spot in a foil of the invention is somewhat less sensitive. However, the data also demonstrate that oxygen concentrations can still accurately and conveniently be determined with a foil of the invention. In addition, a foil of the invention has the advantages that result from the presence of layer L-2, such as the protection that this layer offers to the luminescent compound and the strongly reduced risk of contamination of the contents of the MAP-package.

Besides flexoprinting, foils were also prepared by making use of Continuous Ink Jet Printing (Linx printer). Two km of laminated foil was prepared using yellow printing ink (comprising 1 g of luminescent compound per liter ink) at a printing speed of 400 m/min. The ratio $tau_0/tau$ of the coated foil was 1.32 for the thus produced spots.

The invention claimed is:

1. A multi-layered packaging foil comprising:
   a layer L-1 having an oxygen gas transmission rate OGTR-1 which is 3 cm$^3$ m$^{-2}$ day$^{-1}$ or less;
   a luminescent compound having a property that luminescence of the luminescent compound is capable of being quenched by oxygen; and
   a layer L-2 adhering to the layer L-1 and to the luminescent compound, wherein
   the luminescent compound is present between and is completely enclosed by the layers L-1 and L-2, and wherein
   the layer L-2 has an oxygen gas transmission rate OGTR-2 of 3,000 cm$^3$ m$^{-2}$ day$^{-1}$ or more and is at least 1,000 times higher than the OGTR-1.

2. The multi-layered packaging foil according to claim 1, further comprising a matrix material which comprises the luminescent compound between the layers L-1 and L-2.

3. The multi-layered packaging foil according to claim 2, wherein the matrix material comprises a material selected from the group consisting of polystyrene, silicone gels, nitrocellulose and cellulose acetate butyrate.

4. The multi-layered packaging foil according to claim 1, wherein the OGTR-1 is 1 cm$^3$ m$^{-2}$ day$^{-1}$ or less at 25° C. and 0% RH at 1 atm oxygen partial pressure difference (ASTM D3985).

5. The multi-layered packaging foil according to claim 4, wherein the OGTR-2 is at least 10,000 cm$^3$ m$^{-2}$ day$^{-1}$ at 25° C. and 0% RH at 1 atm oxygen partial pressure difference (ASTM D3985).

6. The multi-layered packaging foil according to claim 1, wherein the layer L-1 comprises a layer of a polymer selected from the group consisting of low-density polyethylene, linear low-density polyethylene, high-density polyethylene, polypropylene, biaxially oriented polypropylene, poly(ethylene-vinyl acetate), poly(ethylene-vinyl alcohol), poly(ethyleneacrylic acid), polystyrene, poly(styrene-1,3-butadiene) oriented polystyrene, poly(vinyl alcohol), poly(vinyl chloride), poly(vinylidene chloride), poly(tetrafluoroethylene), poly(ethylene terephthalate), poly(ethylene naphthalate), polycarbonates, polyamides such as nylon-MXD6, polyacrylonitrile, regenerated cellulose and poly (lactic acid).

7. The multi-layered packaging foil according to claim 1, wherein the layer L-2 comprises a layer of a polymer selected from the group consisting of polyethylene, polypropylene, poly(ethylene-terephthalate) and oriented polyamide.

8. The multi-layered packaging foil according to claim 1, wherein the OGTR-2 is at least 10,000 times higher than the OGTR-1.

9. The multi-layered packaging foil according to claim 1, wherein the luminescent compound is selected from the group consisting of ruthenium(II)-tris-4,7-diphenyl-1,10 phenantroline (Ru-DPP), platinum(II)-meso-tetra(pentafluorophenyl) porphine (Pt-TFPP), palladium coproporphyrin (PdCPP), platinum or palladium octaethylporphyrin (PtOEP,PdOEP), platinum or palladium tetraphenylporphyrin (PtTPP, PdTPP), iridium(III) acetylacetonato-bis(3-(benzothiazol-2-yl)-7-(diethylamino)-coumarin), camphorquinone and erythrosin B.

10. The multi-layered packaging foil according to claim 1, wherein the luminescent compound has a relative luminescence intensity $I_0/I$ or relative luminescence lifetime $tau_0/tau$ of 1.20 or higher, wherein $I_0$ and $tau_0$ represent the luminescence intensity and luminescence lifetime in the absence of oxygen, respectively, and wherein I and tau represent the luminescence intensity and luminescence lifetime in the presence of oxygen, respectively.

11. A method for preparing a multi-layered packaging foil according to claim 1, wherein the method comprises:
   providing a layer L-1 having an oxygen gas transmission rate OGTR-1 of 3 cm$^3$ m$^{-2}$ day$^{-1}$ or less;
   (b1) applying on the layer L-1 a luminescent compound having a property such that luminescence of the luminescent compound is quenchable by oxygen; and then
   (c1) laminating the layer L-1 with a layer L-2 having an oxygen gas transmission rate OGTR-2 of 3,000 cm$^3$ m$^{-2}$ day$^{-1}$ or more such that the layer L 2 completely covers the applied luminescent compound and such that the luminescent compound is completely enclosed by the layers L-1 and L-2;
   or wherein the method comprises:
   (a2) providing a layer L-2 having an oxygen gas transmission rate OGTR-2 of 3,000 cm$^3$ m$^{-2}$ day$^{-1}$ or more;
   (b2) applying on the layer L-2 a luminescent compound having a property such that luminescence of the luminescent compound is quenchable by oxygen; and then
   (c2) laminating the layer L-2 with a layer L-1 having an oxygen gas transmission rate OGTR-1 that is 3 cm$^3$ m$^{-2}$ day$^{-1}$ or less such that the layer L-1 completely covers the applied luminescent compound and such that the luminescent compound is completely enclosed by the layers L-1 and L-2;
   or wherein the method comprises:
   (a3) providing a layer L-2 having an oxygen gas transmission rate OGTR-2 of 3,000 cm$^3$ m$^{-2}$ day$^{-1}$ or more;
   (b3) applying on the layer L-2 a luminescent compound having a property such that luminescence of the luminescent compound is quenchable by oxygen;
   (c3) laminating the layer L-2 with a first layer of a material to produce an intermediate foil, wherein the first layer completely covers the applied luminescent compound; and then
   (d3) applying a second layer on the first layer of the intermediate foil, wherein the second layer has an oxygen gas transmission rate OGTR-1 that is 3 cm$^3$ m$^{-2}$ day$^{-1}$ or less such that the second layer completely covers the first layer.

12. The method according to claim 11, wherein the method comprises dissolving the luminescent compound in a solvent and evaporating the solvent prior to the laminating.

13. A multi-layered packaging foil obtained by the method of claim 11.

14. Packaging comprising the packaging foil according to claim 1.

15. A method for measuring the oxygen content in the packaging according to claim 14, wherein the method comprises:
   (i) illuminating the luminescent compound present in the foil of the packaging with electromagnetic radiation of a wavelength at which luminescence occurs;
   (ii) measuring the intensity or the lifetime of the luminescence of the luminescent compound present in the foil; and then
   (iii) identifying which concentration of oxygen corresponds to the measured lifetime or intensity by use of the Stern-Volmer relationship of the particular foil that is used in the packaging.

* * * * *